(12) United States Patent
Stopek

(10) Patent No.: US 9,463,260 B2
(45) Date of Patent: Oct. 11, 2016

(54) SELF-SEALING COMPOSITIONS

(75) Inventor: Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 1573 days.

(21) Appl. No.: 12/793,776

(22) Filed: Jun. 4, 2010

(65) Prior Publication Data

US 2010/0331880 A1   Dec. 30, 2010

Related U.S. Application Data

(60) Provisional application No. 61/221,246, filed on Jun. 29, 2009.

(51) Int. Cl.

| | | |
|---|---|---|
| *A61B 17/08* | (2006.01) | |
| *A61L 17/14* | (2006.01) | |
| *A61B 17/064* | (2006.01) | |
| *A61B 17/072* | (2006.01) | |
| *A61L 31/14* | (2006.01) | |
| *A61B 17/00* | (2006.01) | |
| *A61F 2/00* | (2006.01) | |
| *A61F 13/00* | (2006.01) | |

(52) U.S. Cl.
CPC ............ *A61L 17/14* (2013.01); *A61B 17/0644* (2013.01); *A61B 17/07292* (2013.01); *A61L 31/14* (2013.01); *A61L 31/145* (2013.01); *A61B 2017/00495* (2013.01); *A61B 2017/00884* (2013.01); *A61B 2017/00898* (2013.01); *A61B 2017/0648* (2013.01); *A61F 2/0063* (2013.01); *A61F 2013/00451* (2013.01)

(58) Field of Classification Search
CPC . A61L 17/14; A61L 31/145; A61B 17/0644; A61B 17/07292; A61B 2017/00495; A61B 17/00884; A61B 17/00898; A61B 17/0648; A61F 2/0063; A61F 2013/00451
USPC .............. 227/175.1; 424/422–424, 443, 444; 606/75, 151, 214, 219, 220; 623/23.72, 623/23.75, 23.76
See application file for complete search history.

(56) References Cited

U.S. PATENT DOCUMENTS

| | | | |
|---|---|---|---|
| 6,165,201 A | 12/2000 | Sawhney et al. | |
| 6,495,127 B1 * | 12/2002 | Wallace et al. ............ | 424/78.03 |
| 6,566,406 B1 | 5/2003 | Pathak et al. | |
| 6,605,294 B2 | 8/2003 | Sawhney | |
| 6,818,018 B1 | 11/2004 | Sawhney | |
| 6,887,974 B2 | 5/2005 | Pathak | |
| 7,009,034 B2 | 3/2006 | Pathak et al. | |
| 7,303,814 B2 | 12/2007 | Lamberti et al. | |
| 7,332,566 B2 | 2/2008 | Pathak et al. | |
| 2003/0135238 A1 | 7/2003 | Milbocker | |

(Continued)

FOREIGN PATENT DOCUMENTS

| | | |
|---|---|---|
| WO | WO 2006/023578 A2 | 3/2006 |
| WO | WO 2010/043979 A2 | 4/2010 |

OTHER PUBLICATIONS

Iossif Strehin et al., "A versatile pH sensitive chondroitin sulfate-PEG tissue adhesive and hydrogel", Biomaterials, vol. 31 (2010) pp. 2788-2797.

(Continued)

*Primary Examiner* — Ashley Fishback

(57) ABSTRACT

Medical devices having a wound closure device and a reinforcing material are reacted in situ to create a self-sealing implant.

7 Claims, 7 Drawing Sheets

(56) References Cited

U.S. PATENT DOCUMENTS

| | | |
|---|---|---|
| 2003/0139771 A1 | 7/2003 | Fisher et al. |
| 2006/0173470 A1 | 8/2006 | Oray et al. |
| 2006/0235469 A1 | 10/2006 | Viola |
| 2007/0089756 A1* | 4/2007 | Nelson et al. ............... 128/898 |
| 2007/0243227 A1 | 10/2007 | Gertner |
| 2008/0110961 A1* | 5/2008 | Voegele et al. ............ 227/179.1 |
| 2008/0114383 A1* | 5/2008 | Hunt et al. ................... 606/153 |
| 2008/0128296 A1 | 6/2008 | Stopek et al. |
| 2008/0220047 A1 | 9/2008 | Sawhney et al. |
| 2009/0324721 A1 | 12/2009 | Kennedy |
| 2010/0076489 A1 | 3/2010 | Stopek et al. |
| 2011/0251699 A1* | 10/2011 | Ladet ........................ 623/23.72 |

OTHER PUBLICATIONS

Ratner et al., eds., Biomaterials Science—An Introduction to Materials in Medicine, $2^{nd}$ Edition, 2004, pp. 100-110.

European Search Report corresponding to European Application No. 10 25 1174.8, dated Jul. 2, 2013; 8 pages.

* cited by examiner

Saline, water or Physiologic Fluids @ pH 7 to 10

Crosslinking reaction.

Saline, water or Physiologic Fluids @pH 7 to 10

SELF-SEALING COMPOSITIONS

CROSS-REFERENCE TO RELATED APPLICATIONS

The present application claims priority to, and the benefit of, U.S. Provisional Patent Application Ser. No. 61/221,246, filed on Jun. 29, 2009, the entire contents of which are hereby incorporated by reference.

TECHNICAL FIELD

The present disclosure relates to self-sealing implants, and more particularly to self-sealing implants comprising a first reactive component and a second reactive component.

BACKGROUND OF RELATED ART

Wound closure devices, such as staples and sutures are commonly used in surgeries, for example, to resect tissues, transect tissues, and to create connections between tissues and organs. More particularly, wound closure devices such as surgical staplers are provided in several iterations including linear, circular, curved, for various types of surgeries including vascular, bariatric, thoracic and gynecologic.

Fluid (e.g., air and blood) leaks have been reported for certain procedures. One solution includes the use of an additional reinforcement such as a buttress. Buttresses or pledgets may be applied to the staple line to provide reinforcement to the staple line and/or reinforcement to delicate tissue. In use, staples or sutures are currently fired or sewn through a buttress. However, a need exists for suture or staple compositions which complement reinforcing materials, thereby reducing leak potential.

SUMMARY

Self-sealing implants of the present disclosure include at least one wound closure device and a reinforcing material, wherein the wound closure device comprises a first reactive component and the reinforcing material comprises a second, complementary reactive component. More specifically, the wound closure device may include staples, sutures, clips, tacks, screws, pins, anchors, fasteners, sheaths, shunts, tissue barriers, stents and grafts. The reinforcing material may include tapes, felts, scaffolds, patches, pledgets, mesh, and buttresses.

In some embodiments, at least one of the first and second reactive components comprise a self-sealing device coating. In other embodiments, at least one of the first and second reactive components is selectively deposited on the self-sealing device.

The first reactive component and the second reactive component may be selected from the group consisting of electrophilic functional groups and nucleophilic functional groups. More specifically, the first reactive component and the second reactive component may comprise a material selected from the group consisting of succinimidyl containing polymers and multifunctional primary amines.

The interaction of the first reactive component and the second reactive component may result in a hydrogel.

In alternate embodiments, the self-sealing device includes at least one staple and a buttress, wherein upon interaction of the at least one staple and the buttress, a hydrogel is formed. The staple may further comprise a coating including materials selected from the group consisting of succinimidyl containing polymers and multifunctional primary amines. The buttress may also comprise a material selected from the group consisting of succinimidyl containing polymers and multifunctional primary amines.

The self-sealing device may comprise natural and synthetic materials such as polyesters, poly ether esters, poly orthoesters, polyhydroxyalkoanates, polyhydroxybutyrates, polyanhydrides, polyamines, polyamide esters, polycarbonates, silicones, polymer drugs, collagen, derived collagen, bovine pericardium, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitin, chitosan, casein, alginate and combinations thereof.

A method for creating a self sealing device in situ is included, comprising the steps of positioning a buttress on a tissue, firing at least one staple from a stapler, the at least one staple contacting the buttress and, initiating a chemical reaction.

BRIEF DESCRIPTION OF FIGURES

Various embodiments of the present disclosure are described hereinbelow with reference to the drawings, wherein.

DETAILED DESCRIPTION

The present disclosure is directed to medical implants that are self-sealing. In particular, the self-sealing implants include wound closure devices comprising a first reactive component and a reinforcing material comprising a second, complementary reactive component. The first and second reactive components are disposed on or within the devices in an unreacted state. In embodiments, the first reactive component is selectively reacted in situ with a second, complementary reactive component. More specifically, upon interaction or physical contact, the first component and the second component react. In certain embodiments, physiologic fluids or solutions such as water or saline (at adjusted pH or iconicity) may assist in initiating a reaction between the two components.

As used herein, the term "tissue" includes, but is not limited to, tissues such as lung, bowel, skin, fat, fascia, bones, muscles, tendons, ligaments, solid organs, lumens, ducts, lymphatics, nerves, and blood vessels.

As used herein, the term "physiologic fluid" includes, but is not limited to fluids such as blood, plasma, peritoneal fluid, cerebral spinal fluid, urine, lymph fluid, synovial fluid, vitreous fluid, saliva, gastrointestinal luminal contents, bile, and gas (e.g., $CO_2$).

The term "complementary" as used herein, means the second reactive component is chemically tailored to selectively or preferentially react with the first reactive component. In other words, individually, the two components are stable, but when paired together (in situ), a chemical reaction is initiated. More specifically, the first reactive component will not undergo a substantive chemical change without contacting the complementary second component. Once physically contacted in situ, both reactive components undergo a chemical change (e.g., forming a cross-linked polymer) creating a self-sealing implant.

Figure 1:
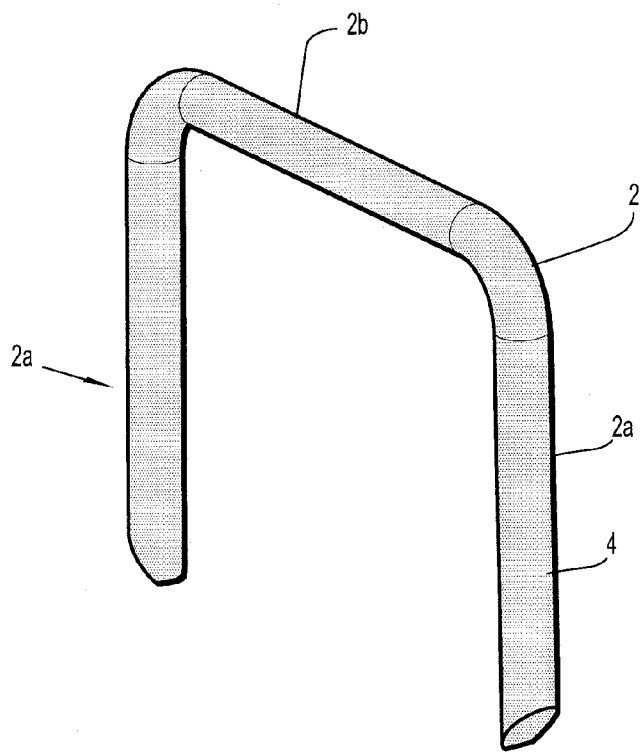
FIG. 1 is a side perspective view of a surgical staple including a staple coating.
Figure 2:
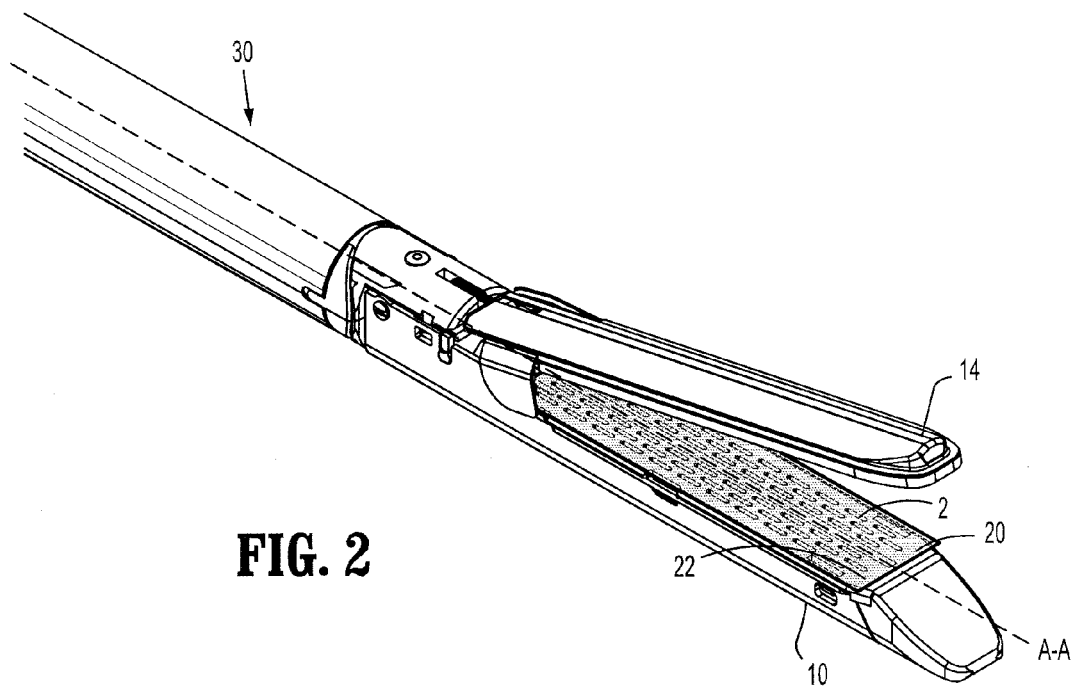
FIG. 2 is a side perspective view of a surgical stapler including a reinforcing material.
Figure 3:
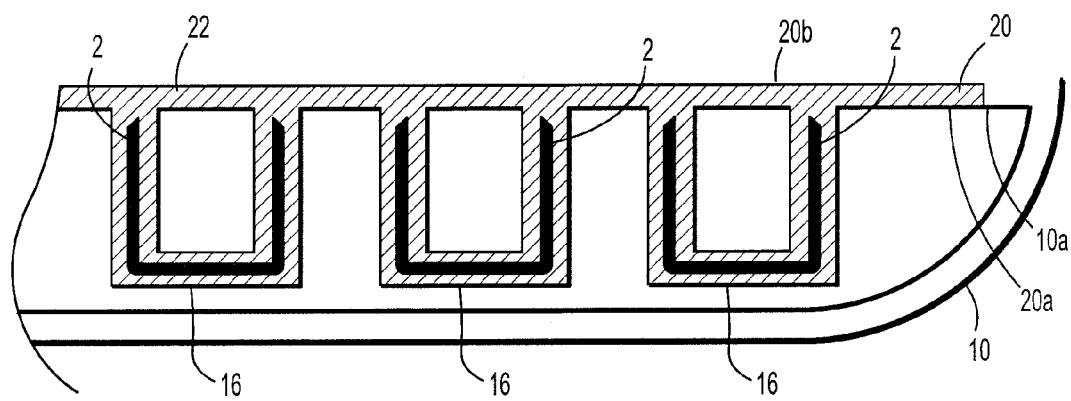
FIG. 3 is a cross-sectional view of a surgical staple cartridge along line A-A of FIG. 2, including staples.

In general, self-sealing implants comprise a reinforcing material including a first reactive component while the wound closure device comprises a second, complementary reactive component. FIGS. 1-3 illustrate one embodiment of the present disclosure including a staple 2 (wound closure device) coated with a first reactive component which is paired in situ with a buttress 20 (reinforcing material) including the second, complementary reactive component. More specifically, FIG. 1 illustrates the staple 2 which is coated with a first reactive component 4. In general, staple 2 includes staple legs 2a, connected therebetween by a staple backspan 2b. The first reactive component 4 is illustrated in the form of a coating, although the first reactive component may be present on the staple in other forms, including but not limited to compounding the reactive component within a polymer resin, selective application of localized depots of a reactive component, or otherwise embedding an unreacted, first reactive component within the self-sealing device. Staples 2 may be coated, for example, using a dip coating technique, although other coating methods are within the purview of those skilled in the art and will be discussed later. As illustrated, the entire staple 2 is coated, however it is also envisioned that only a portion of the staple 2 may be coated. For example, in certain embodiments, the staple legs 2a may be coated while the staple backspan 2b remains uncoated. In alternate embodiments, the staple may have a patterned coating disposed thereon for selective surfaces of the staple to crosslink with second reactive component (and/or tissue). It is also envisioned that different rows of staples (in a surgical stapler, such as an EndoGIA™ from Covidien, North Haven, Conn.) may have different reactive components or may include different patterns of reactive components on the staple surface. For example, it may be useful for the interior-most row of staples to have a higher degree of crosslinking (to the reinforcing material and/or tissue), while the outer-most row of staples has a lesser degree of crosslinking (to the reinforcing material and/or tissue).

Moving to FIGS. 2-3, a plurality of staples 2 are positioned in a loading unit 30 for firing the staples 2 into tissue. FIG. 2, illustrates a buttress 20 includes a second, complementary reactive component. The buttress 20 is illustrated, for example, as a single polymer laminar sheet, it being understood that the buttress is not limited to a single laminar sheet. The second, complementary reactive component 22 is illustrated in the form of a coating, although the second, complementary reactive component 22 may be present on the buttress 20 in other forms such as compounding within the resin, selective weaving of threads/filaments within the buttress, or selective application of localized depots of a reactive component. Buttress 20 may be coated using any technique within the purview of those skilled in the art. As illustrated, the entire buttress 20 is coated, however it is also envisioned that only a portion of the buttress 20 may be coated. For example, in certain embodiments, a first surface 20a of the buttress may include a reactive component, while a second surface 20b does not include the reactive component. In alternate embodiments the first and second surfaces of the buttress may be coated or otherwise contain different reactive components. For example, a first surface 20a may be coated with a second reactive component (to react with the first reactive component), while the second surface 20b may be coated with a third reactive component to selectively crosslink to the tissue surface. The reinforcing material may also have the second reactive coating selectively patterned on the surface or selectively incorporated/positioned within the reinforcing material (e.g., localized depots).

The buttress 20 is positioned adjacent the staple cartridge 10 (FIGS. 2-3) however, it is also contemplated that the buttress 20 be positioned with respect to the anvil 14, or the buttress 20 may be positioned with respect to both the cartridge 10 and the anvil 14. It is also envisioned that the buttress 20 may be provided pre-loaded on the loading unit 30 or, in the alternative, the buttress 20 may be attached to the loading unit 30 in the operating room prior to implantation. One example of an integrated buttress which may be employed is DUET TRS™ (Covidien, North Haven, Conn.), disclosed in U.S. Provisional Patent Application No. 60/905, 532, filed Mar. 6, 2007, the entire disclosure of which is incorporated by reference herein.

Figure 4A:
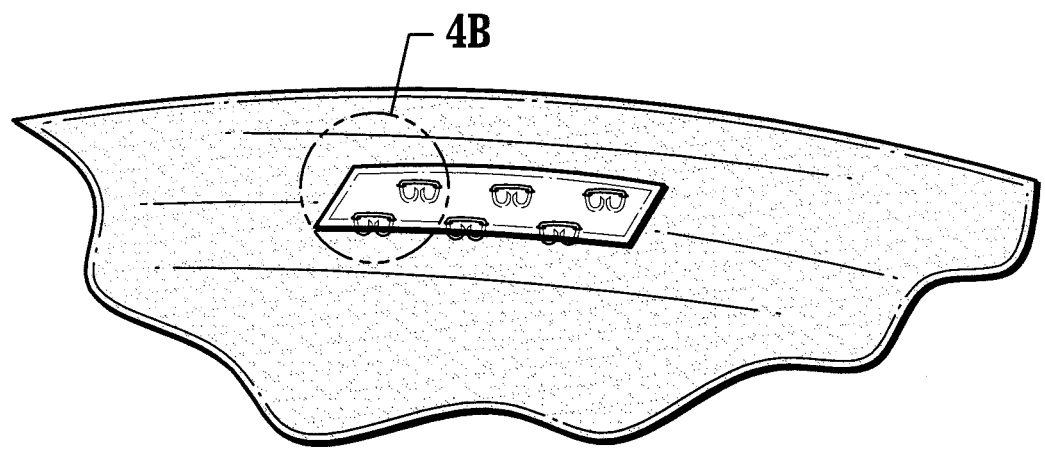
FIG. 4A is a perspective view of one embodiment of the present disclosure, illustrating staples fired through a buttress into tissue.
Figure 4B:
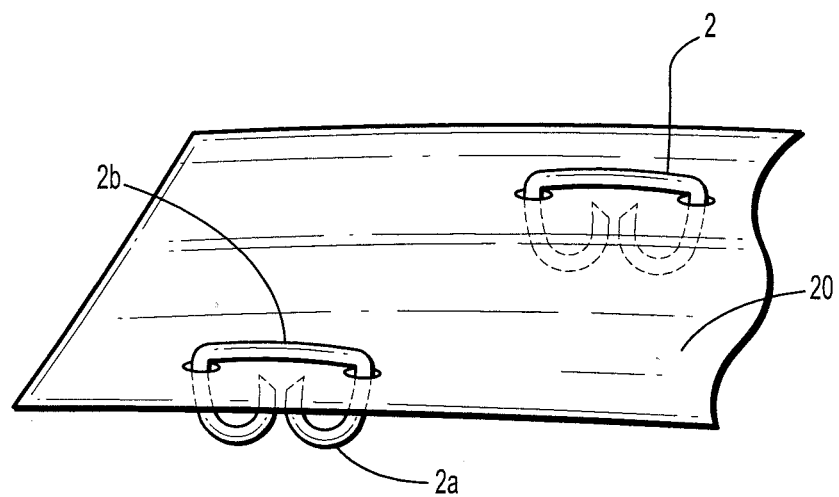
FIG. 4B is an enlarged view of a portion of FIG. 4A.

FIG. 3 illustrates another view of a row of staples 2 in the staple pockets 16 taken along line "A-A". The buttress 20 is placed adjacent the cartridge surface 10a such that when the staples 2 are fired, the staples' legs 2a first penetrate the buttress 20, then pierce a first tissue surface (not shown), the staple legs 2a next exit a second tissue surface (not shown), where the staple legs 2a contact the staple buckets (not shown) on the anvil 14, bending the staple legs 2a back into the second tissue surface, completing a substantially "B" shaped staple formation as illustrated in FIGS. 4A-4B. As the staples 2 are fired through the buttress 20 in situ, physiologic fluids mix the first and second reactive components together, initiating a chemical reaction, resulting in a self-sealing implant.

Within seconds to several minutes, the first reactive component and the second reactive component have chemically reacted, creating a self-sealing implant. Once the unreacted components are physically contacted in situ, the two components mix and form a crosslinked polymer network. Physiologic fluids or moisture from the body cavity may assist in mixing of the two reactive components. Once the crosslinked polymer network (hydrogel) has formed, the swollen hydrogel seals any void space present. For example, the hydrogel present on the staple legs may swell, sealing off any void space within the tissue or buttress.

Figure 5A:
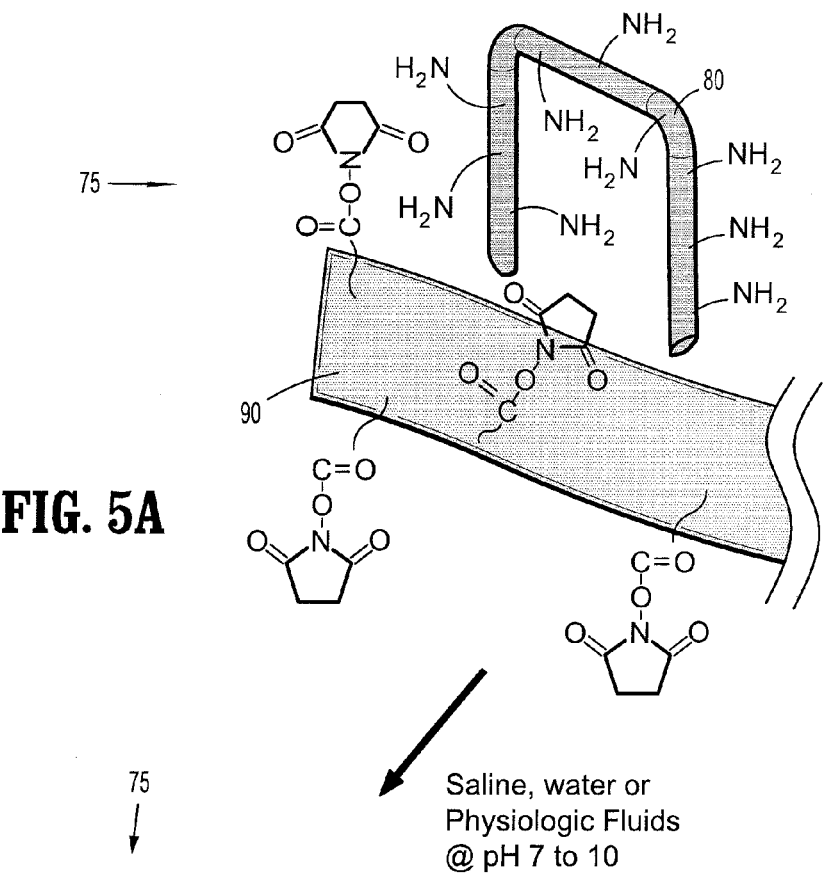
FIGS. 5A-5B are side perspective views illustrating one embodiment of the present disclosure in which the reactive groups are NHS ester groups and primary amines.
Figure 5B:
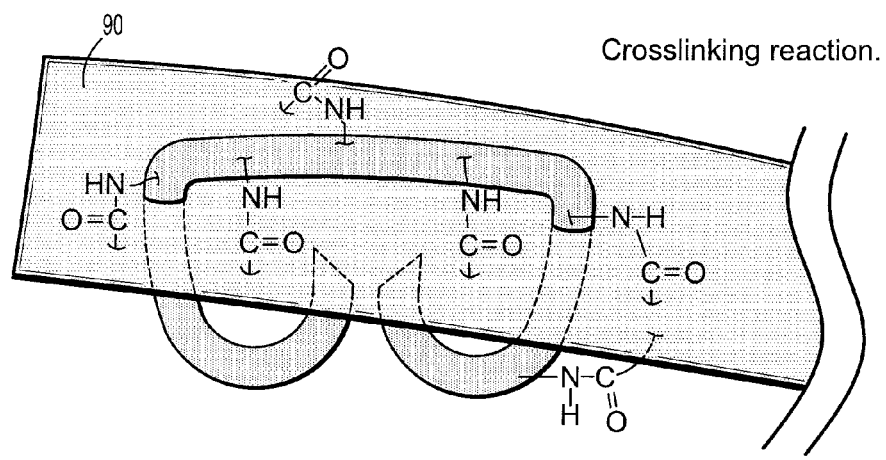

More specifically, in one embodiment illustrated in FIG. 5, the self-sealing implant 75 includes a staple 80 having several primary amines groups tethered to the surface. The primary amines may be in the form of a coating or other means of chemically attaching/depositing functional groups on the surface of the device 80. A reinforcing material 90 is illustrated with succinimidyl functional groups attached to the surface. Again, these functional groups may be attached to the surface or embedded within the device using various means detailed in the present disclosure. Once the staple 80 and the reinforcing material 90 are contacted in situ, in the presence of moisture including water, saline or other physiologic fluids in a given pH range of about 7 to about 10, in embodiments, from about 7.5 to about 9, the two reactive components crosslink. The self-sealing device 75 is created (FIG. 5B) in which the two reactive components chemically crosslink the reinforcing material 90 and the staple 80 to each other, creating a hydrogel. Additionally, the hydrogel may uptake additional fluids from the surrounding environment, sealing any void space found in the surrounding area. The resultant hydrogel may degrade via hydrolysis, releasing water soluble fragments overtime. The self-sealing implant may be chemically modified to degrade in a preferred time range, for example, from about 1 day to about 30 days.

Figure 6A:
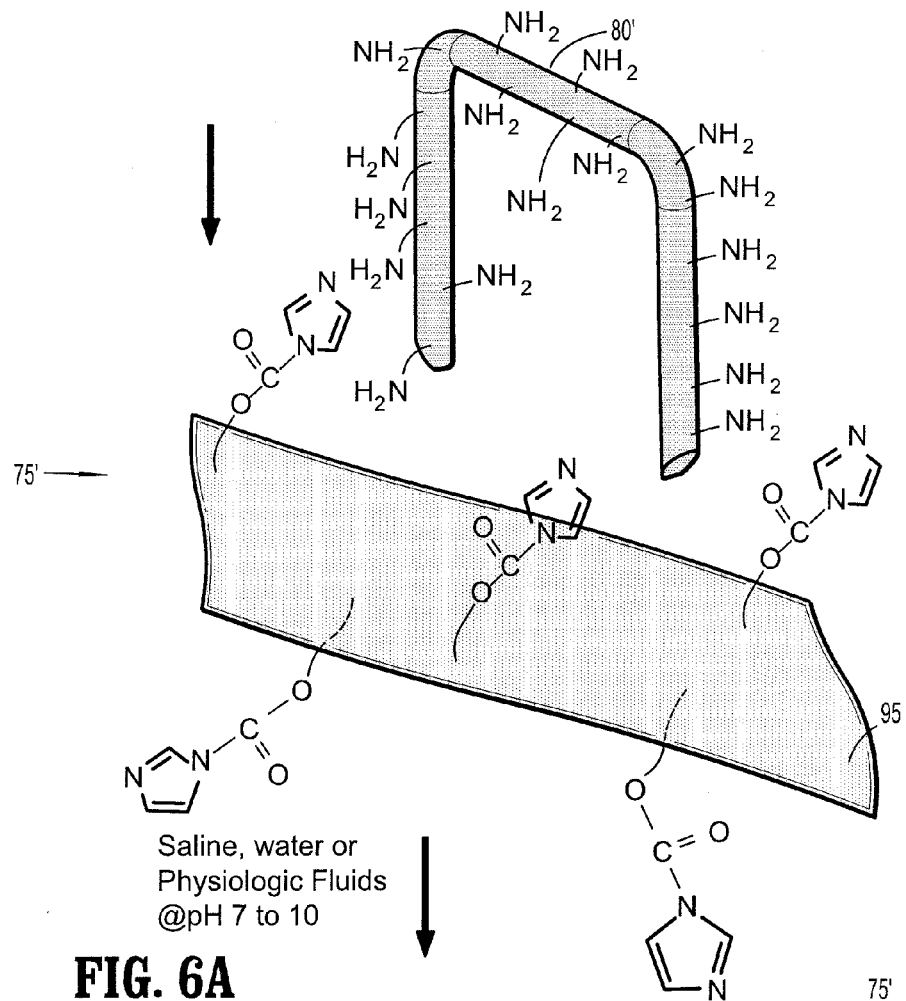
FIGS. 6A-6B are side perspective views illustrating one embodiment of the present disclosure in which the reactive groups are carbodiimide groups and primary amines.
Figure 6B:
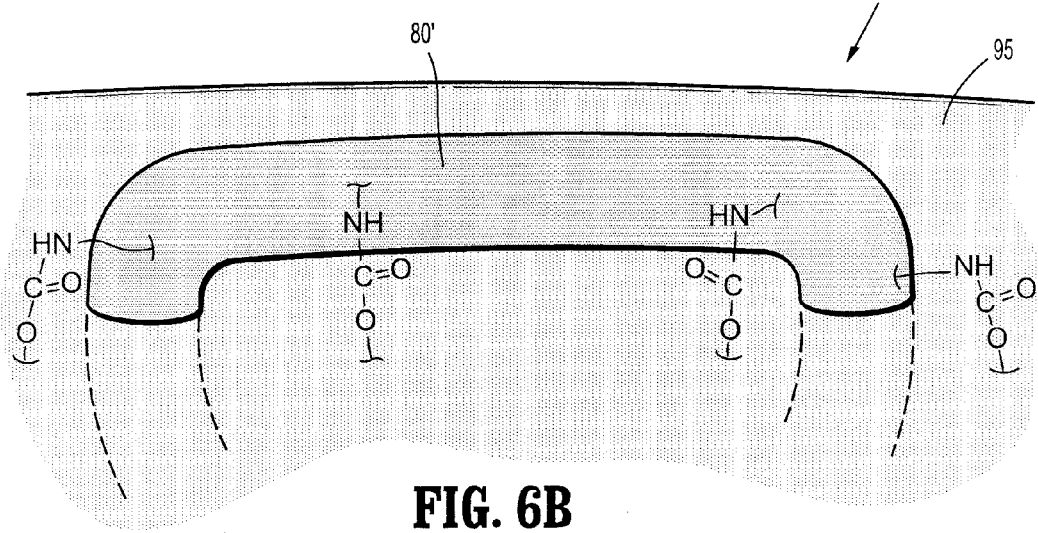

FIGS. 6A-6B illustrate a similar embodiment to FIGS. 5A,5B therefore all parts which are similar will be designated with a prime mark and only the differences will be described below. A staple 80' is illustrated having multifunctional primary amine groups positioned on a surface thereof. A reinforcing material 95 is illustrated with carbodiimide functional groups attached to the surface. Once the staple 80' and the reinforcing material 95 are contacted in situ, the presence of moisture including water, saline or other physiologic fluids in a given pH range of about 7 to about 10, in embodiments, from about 7.5 to about 9, the two reactive components crosslink. The self-sealing device 75' is created (FIG. 6B) in which the two reactive components chemically crosslink the reinforcing material 95 and the staple 80' to each other, creating a hydrogel.

The first or second reactive components of the present disclosure may comprise natural or synthetic multifunctional primary amines. The term "multifunctional" as used herein means the primary amine includes at least two primary amine groups. In one example, a multifunctional primary amine may comprise a coating on the wound closure device, it being understood that the multifunctional primary amine may be incorporated into the self-sealing implant utilizing several methods which will be later detailed. In another example, the reinforcing material may comprise in entirety, an aminated dextran scaffold, which is selectively reactive with succinimidyl functional polymer. Suitable natural or derived primary amines are found in materials (including tissues) such as collagen, albumin, elastin, polysaccharides such as chitosan, aminated dextran, modified cellulose and hyaluronic acid, polylysine or peptides and/or proteins with lysine residues (including pegylated or macromers versions), polyarginine or peptides and/or proteins with arginine residues (including pegylated or macromers versions), polyhistidine or peptides and/or proteins with histidine residues (including pegylated or macromers versions) and combinations thereof. Suitable synthetic amines include vinyl monomers with primary amine functionality (e.g., acrylamide) and copolymers thereof, lysine modified polyesters (PLA), polyethylene glycol (PEG), PEG polypropylene glycol, PEG-co-silicone and combinations thereof. Other suitable multifunctional amines include those listed above.

Additional suitable first or second reactive components comprise materials including succinimidyl functional polymers such as N-hydroxysuccinimide esters (NHS), N-hydroxysulfosuccinimide esters (SNHS), N-hydroxyethoxylated succinimide esters (ENHS) and combinations thereof. Succinimidyl-based esters are reactive with the above-mentioned multifunctional primary amines. In general, it should be understood that if the wound closure device comprises a NHS ester reactive group, the second complementary reactive group comprises a multifunctional primary amine presenting surface.

In further embodiments, the first or second reactive component may comprise electrophilic functional groups while the complementary second or first component may comprise nucleophilic functional groups. Electrophilic functional groups include the succinimidyl containing polymers listed above such as SNHS and ENHS. Additional non-limiting examples of electrophilic groups include carbonylimidazoles, isocyanates, vinylsulfones, maleimides, and p-nitrophenyls. Suitable nucleophilic functional groups include natural and synthetic multifunctional primary amines such as those listed above in addition to thiol groups. Other suitable first and second nucleophilic and electrophilic reactive components and methods of making are disclosed in U.S. Pat. Nos. 6,887,974; 7,332,566; 6,566,406; 7,009,034; 6,165,201; 6,818,018 and U.S. Patent Application 61/078,968 filed on Jul. 8, 2008 the subject matter of which is incorporated by reference herein.

The first and second reactive components utilized to form hydrogels of the present disclosure may have biocompatible and water soluble core groups. As used herein, water soluble refers to a solubility of at least about 1 g/l in water. This core group may be a water soluble molecule with a minimum of three arms. An arm of a core group refers to a linear chain of chemical groups that connect a crosslinkable functional group to a multifunctional center which initiates the polymerization of the polymeric arms. The combination of this multifunctional center and the attached arms may form the core group.

In embodiments, the core group may be a water soluble polymer. Examples of such polymers that may be used include, for example: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers; vinyl polymers such as polyvinyl alcohol ("PVA") and poly (vinyl pyrrolidinone) ("PVP"); proteins such as poly (amino acids); polysaccharides such as dextran, as well as derivatives of the foregoing and combinations of the foregoing.

In other embodiments, multifunctional centers may include polyols which, in embodiments, may possess hydroxyl groups for initiation of monomeric groups that may form the arms of the core that can then be functionalized with crosslinkable groups. Depending on the desired number of arms, the polyol may possess from about 3 to about 12 hydroxyl groups, in embodiments from about 4 to about 10 hydroxyl groups. The polyol may also possess other protected or unprotected functional groups. Suitable polyols include glycerol, mannitol, reducing sugars such as sorbitol, pentaerythritol, and glycerol oligomers including hexaglycerol, as well as derivatives thereof and combinations thereof. As would be readily apparent to one skilled in the art, the number of hydroxyl groups should be equivalent to the number of arms on the multi-armed core, i.e., the particular polyol chosen should determine the number of arms on the resultant multifunctional core group. In embodiments, a polymer described above, such as polyethylene glycol, may be formed by initiating the polymerization of ethylene oxide with the polyol, thereby forming arms of a multi-armed core that may be further functionalized with reactive components.

Thus hydrogels can be made from a multi-armed core with a first set of functional groups and a low molecular weight polymer having a second set of functional groups. The number of arms on the multi-armed core may be from about 3 to about 12, in embodiments from about 5 to about 10.

For example, a multi-armed core may have hydrophilic arms, e.g., polyethylene glycol, terminated with N-hydroxy succinimide (reactive component), with the combined molecular weight of the arms being from about 1,000 to about 40,000; artisans will immediately appreciate that all ranges and values within the explicitly stated bounds are contemplated. In some embodiments, it may be desirable to utilize a multi-armed core having six arms or eight arms. The molecular weight of an individual arm may be from about 250 to about 5000, in embodiments from about 1000 to about 3000, in other embodiments from about 1250 to about 2500.

In some embodiments, six-armed or eight-armed polymer cores may be reacted with a low molecular weight polymer such as trilysine as a first reactive component. The trilysine provides multiple points of reaction for crosslinking a second reactive component and it presumably (without being limited to a particular theory of action) allows relatively little movement in terms of shrinking or swelling, with such movement probably being related to the multi-armed cores, which are relatively larger and more mobile. Accordingly, other small molecules may be used instead of trilysine, for example, molecules with a molecular weight of from about 100 to about 5000, in embodiments from about 300 to about 2500, in other embodiments from about 500 to about 1500. Such small molecules may have at least about three functional groups, in embodiments from about 3 to about 16 functional groups; ordinary artisans will appreciate that all ranges and values between these explicitly articulated values are contemplated. In some cases dilysines and/or tetralysines may be utilized as the low molecular weight precursor.

In some embodiments, the self-sealing device may additionally include a pH activating agent. The pH activating agent may create a localized change in pH after exposure to an aqueous environment to accelerate or initiate hydrogel formation. For example, the pH activating agent may include solid borate crystals such as $Na_2B_4O_7.10H_2O$ although other salt-based or other materials may be employed. In the alternative, pH altering agents may be employed such as, for example, sodium borate, sodium bicarbonate, and the like. The pH activating/altering agent may be loaded into the device utilizing various methods including but not limited to coatings, compounding in the device, applying as an adhesive layer, application of localized depots along the device, and the like.

Figure 7A:
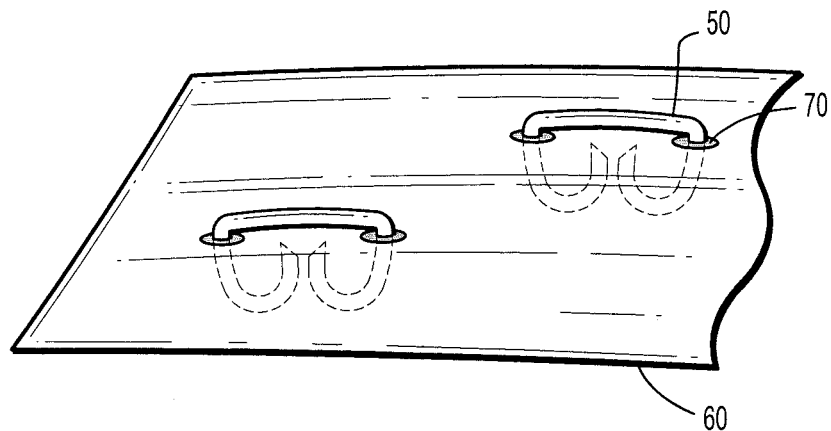
FIG. 7A is a side perspective view illustrating one embodiment according to the present disclosure.
Figure 7B:
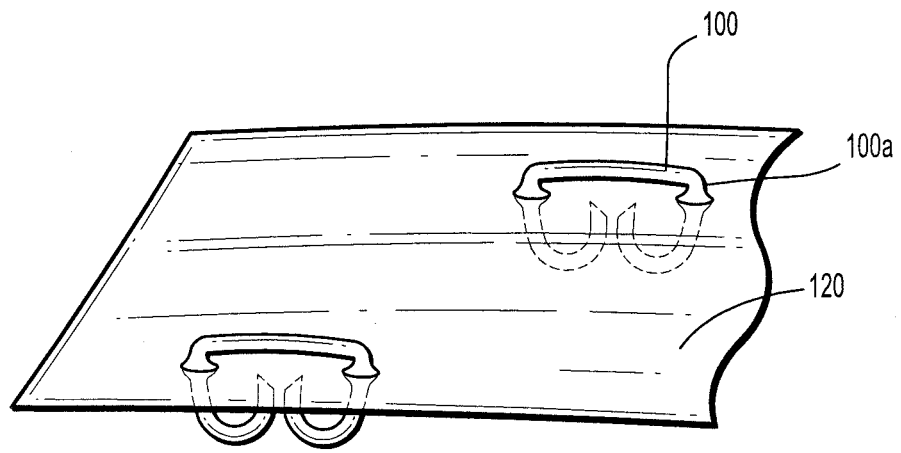
FIG. 7B is a side perspective view illustrating another embodiment according to the present disclosure.

FIGS. 7A-7B illustrate two embodiments of the present disclosure, after the two components have reacted to create a self-sealing device. More specifically, FIG. 7A illustrates a wound closure device 50 (staple) having a first reactive component, fired through a reinforcing material 60 which includes a second reactive component. FIG. 7A illustrates one embodiment of the self-sealing device, resulting in a hydrogel 70 formation between the staples 50 and the buttress 60. Once the two reactive components are mixed, a crosslinked structure is formed in regions adjacent to where physical contact between the first and second reactive components occurs. The new crosslinked structure may be illustrated by presence of a hydrogel formation. In some embodiments in weakened or otherwise damaged tissue, the hydrogel 70 may seal any residual space in the surrounding tissue. Additionally, the hydrogel may be space filling and can be tailored to preferentially swell in specific locations. For example, a hydrogel which has greater swelling properties, such as a 4-armed PEG hydrogel, may be preferentially positioned in the self-sealing device to uptake increased fluids, as compared to an 8-arm PEG hydrogel (which would exhibit less swelling). Overtime, the hydrogel may uptake additional fluids from the surrounding tissue.

FIG. 7B illustrates another embodiment in which the staple legs 100a exhibit more swelling compared to the buttress 120. In both embodiments, the hydrogel forms in the area immediate and generally concentric to the staple legs and may overlap at the interface between the staple and reinforcing material. Depending on the materials selected for the first and second reactive components, either the reinforcing material or the wound closure device may exhibit different and varying degrees of swelling (including negative swelling) or fluid uptake. Examples of materials having different or varying degrees of swelling are disclosed in U.S. Provisional Patent Application No. 11/714,028, filed Mar. 5, 2007, the entire disclosure of which is incorporated by reference herein. For example, an interior or proximal row of staples may swell more, creating more hemostasis closer to the wound, than an exterior/distal row is staples. It is also envisioned that the reinforcing material may preferentially swell is certain locations.

As illustrated in FIGS. 7A-7B, the chemical reaction (of the first reactive component and the second reactive component) includes the formation of a hydrogel. The term hydrogel as used herein includes materials which absorb solvents (such as water), undergo rapid swelling without discernable dissolution, and maintain three-dimensional networks capable of reversible deformation. Hydrogels are traditionally water-swollen, crosslinked polymer structures which include either covalent bonds, ionic crosslinks, physical crosslinks from entanglements, association bonds such as hydrogen bonding or strong van der Waals interactions, or crystallites of two or more macromolecular chains. Crosslinks indicate connection points within the hydrogel structure which may be carbon atoms, but crosslinks may also be small chemical bridges. Crosslinks may also be an association of macromolecular chains due to van der Waals forces or an aggregate formed by hydrogel bonding. Hydrogels may also include crosslinks which may be permanent or semipermanent physical entanglements, or ordered chains which form crystallites.

Hydrogels may be homopolymer hydrogels, copolymer hydrogels (produced by crosslinking of two or more monomer units, one of which must be hydrophilic), multipolymer hydrogels (produced by reaction of three or more comonomers), or interpenetrating polymer hydrogels (produced by preparing a first network that is then swollen in a monomer) (Biomaterials Science, $2^{nd}$ edition, 2004, pp 100-107).

In some embodiments of the present disclosure, materials which constitute "smart hydrogels" may be utilized. Smart hydrogels include materials whose swelling behavior is dependent on the external environment, such as the body. For example, hydrogels may swell (or shrink) with response to factors including but not limited to pH, temperature, ionic strength, enzymatic or chemical reactions, and electrical or magnetic stimuli. The ability of smart hydrogels to rapidly respond to stimuli readily lends these hydrogels to drug delivery applications.

Figure 8:
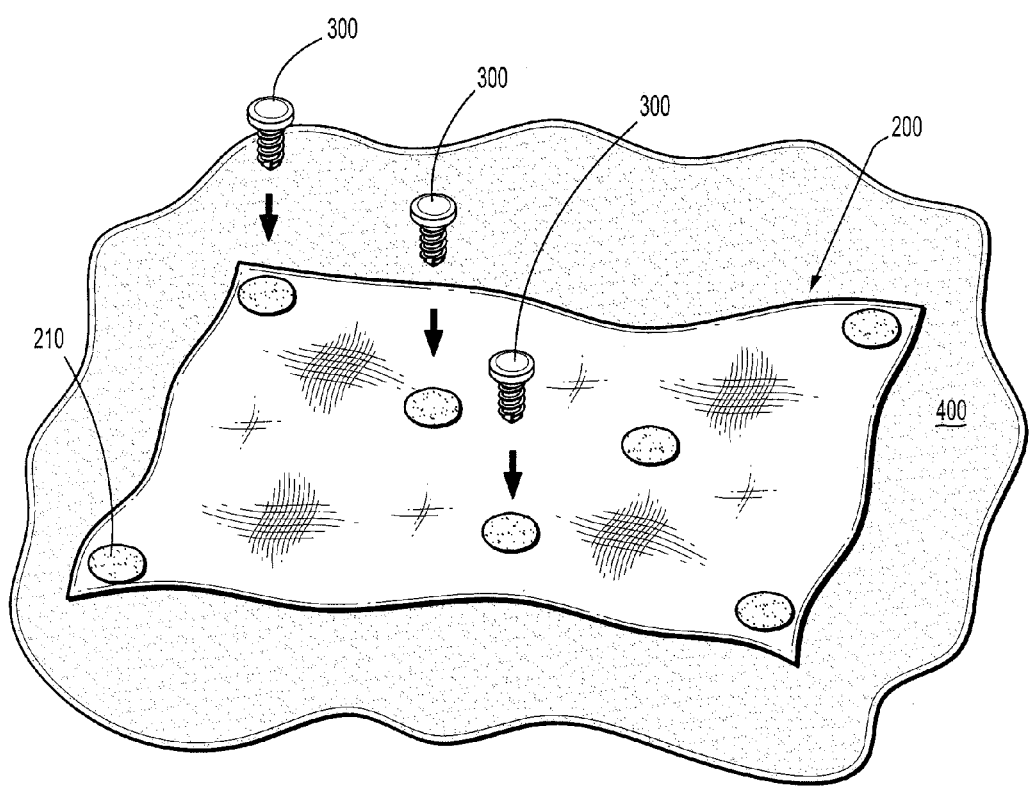
FIG. 8 is a plan view of another embodiment according to the present disclosure.

In alternate embodiments, the first reactive material may be present in specified depots on the device or incorporated within interstices of the device to selectively react with the second complementary reactive component. As illustrated in FIG. 8, a woven mesh 200 includes a first reactive component, for example succinimidyl functional reactive groups, at specified interstices 210 along the mesh surface. The succinimidyl functional groups may be woven within the mesh, deposited at specific interstices of the mesh, or otherwise incorporated therein. Tacks 300 which interact with the mesh 200 are coated with a second reactive component, for example lysine residue. As the tacks 300 are fired through the mesh 200, securing the mesh 200 to tissue 400, the first reactive component and the second reactive component interact, creating sealed regions along the mesh 200 which assist with securing the mesh 200 in place.

In another example, the reinforcing material or the wound closure device may contain depots or reservoirs which can be filled with a specific reactive group. For example, a particulate coating may be used to generate reservoirs or areas with a concentrated amount of a reactive component on the surface of the self-sealing implant. In another example, depots may be created by manufacturing a void or empty space within the device, which may be later filled with the reactive component. The voids may be open or closed cell networks. Method for manufacturing include methods such as machine cutting (such as laser cutting), lyophilization, particulate leaching, compression molding, phase separation, gas foaming (e.g., internal blowing agents such as $CO_2$), or through the use of a porogen (e.g., salt particles). The voids may be filled with a reactive component using methods such as injection molding, or standard coating techniques including those listed above.

Self-sealing implants of the present disclosure include both solid and porous structures. Porous structures may be open or closed-cell foams, prepared using techniques within the purview of those skilled in the art. Porous structures include but not limited to woven fabrics such as mesh, felts, grafts and foam including lyophilized foams or scaffolds. Additionally implants may be constructed from at least one layer. In some embodiments, implants may include multilaminate structures such as foams or films. One non-limiting example of a multilaminate structure includes a woven surgical mesh further including an anti-adhesion coating. In other embodiments, coatings may be further applied to implants of the present disclosure to improve performance characteristics such as lubricity, surgeon handling, wettability, tissue integration and the like. For example, a reinforcing material may be coated with a water soluble layer, such as poly vinyl pyrrolidone (PVP). As the PVP solublizes (within second to minutes) reactive components may be released into the surrounding area, creating a self-sealing implant.

In another example, a collagen buttress (reinforcing material) may be applied to lung tissue using staples coated with an SNHS ester polymer as a first reactive component. In this embodiment, the first reactive component may selectively interact with the collagen buttress (the collagen contains multifunctional primary amines) in addition to reacting with lung tissue. It should be noted that as the lung tissue also includes primary multifunctional amines, the lung tissue would also selectively interact with the staples.

In the description that follows, the term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

In addition to reactive components, other materials used to construct self sealing implants may comprise biodegradable materials such as synthetic and natural materials. For example, the reinforcing material illustrated in FIG. 1 may comprise a glycolide, TMC, dioxanone copolymer which is further coated with a reactive component, it being understood that the reinforcing material is not limited to a specific polymer or copolymer. Suitable synthetic biodegradable materials include polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof.

Polymer drugs referenced hereinabove may include polymers wherein the backbone comprises a polymer drug, or in the alternative, polymer drugs may comprise polymers in which the pendant groups or side chains comprise polymer drugs. In one example, a reinforcing material (e.g., a buttress) may comprise an extruded film of an anti-inflammatory composition such as polyaspirin. Degradable polymer drugs may also comprise polymers including but not limited to polyanhydrides, polyesters, poly ether esters, polyamines, polyamide esters and combinations thereof.

Natural polymers may also be used to construct self-sealing implants of the present disclosure, including but not limited to, collagen, poly (amino acids), polysaccharides such as cellulose (including carboxymethyl cellulose), dextran, chitin, chitosan, alginate and glycosaminoglycans, hyaluronic acid, gut, copolymers and combinations thereof. Collagen as used herein includes natural collagen such as animal derived collagen, or synthetic collagen such as recombinant collagen. Proteins such as elastin, albumin, casein, may also comprise the present disclosure. Additionally, natural materials include chemical modifications of the above-listed materials such as recombinant, aminated, sulfonated, and carboxylated polymer analogs.

In certain applications, it may be preferred to have at least one of the reinforcing material and wound closure device comprise non-biodegradable materials. In one non-limiting example, it may be preferable to have a non-biodegradable would closure device. Suitable materials include fluorinated polymers (e.g., fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyethylene glycol, polyaryletherketone, copolymers and combinations thereof. Additionally, non-biodegradable polymers and monomers may be combined with each other and may also be combined with various biodegradable polymers and monomers to create the self-sealing implant.

In certain embodiments, self-sealing implants according to the present disclosure may be constructed at least in part using shape memory polymers. Shape memory polymers are smart materials which have to ability to return from a deformed state (temporary shape) to their original (permanent) shape induced by an external stimulus such as temperature, current, light, pH, etc. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

In other embodiments, metals or metal alloys may comprise at least the wound closure device, e.g., staples or sutures. Suitable metals and metal alloys may be selected from the group consisting of titanium, nickel titanium, steel, magnesium-based alloys, manganese based-alloys and combinations thereof. Metals or metal alloys of the present disclosure may additionally have shape memory characteristics, or in the alternative, may be biodegradable.

In some diseased patient populations, certain tissues may be less elastic than other tissues. For example, if a patient is diabetic or has undergone chemotherapy treatments, their tissue may be less elastic compared to an otherwise healthy patient. Depending on the staple size, tissue properties and the reinforcing material chosen, the elastic response of the tissue and the reinforcing material vary. Small holes may be present in the buttress and potentially the tissue in the area concentrically surrounding the staple legs. Some embodiments of the present disclosure assist in sealing these small holes, which may prevent fluid leaks. Embodiments of the present disclosure may also increase stabilization of the reinforcing material in tissue. In other embodiments, the self-sealing devices may act as a hemostat, promoting blood clotting or assist in promoting the clotting cascade.

The first and second reactive components may be applied to implants or incorporated therein using a variety of methods. In one embodiment, wound closure materials and/or reinforcing materials may include reactive components in the form of a coating. Methods for coating medical implants are within the purview of those skilled in the art and include but are not limited to spraying (i.e., ultrasonic or electro-spraying), brushing, dipping, drip coating, solvent evaporation, laser and inkjet printing, and the like. The coating compositions may be in the form of a solution, dispersion, emulsion or any other homogeneous or heterogeneous mixture. Additionally, solvents may be used to apply coatings to the implants. Suitable solvents are within the purview of those skilled in the art which include both polar and non-polar solvents.

The first and second reactive components may also be incorporated into the device utilizing other methods, for example, the reactive component may be embedded or compounded within the resin. For example, a multifunctional primary amine may be compounded within polyester and extruded (or coextruded) to create an implant such as a fiber. Additionally, such fibers may be braided or interwoven with other fibers to create a multifilament implant such as a braided suture or a mesh. The plurality of filaments may be combined using any technique within the purview of one skilled in the art such as commingling, twisting, braiding, weaving, entangling, and knitting. For example, a plurality of filaments may simply be combined to form a yarn. As another example, a plurality of filaments may be braided.

As previously discussed, self sealing implants of the present disclosure include at least one reinforcing material and one wound closure device. Exemplary reinforcing materials include, but are not limited to, reinforcing devices such as pledgets, buttresses, patches, scaffolds, tapes, felts, and mesh (including biologic and composite mesh). Suitable wound closure devices of the present disclosure include but are not limited to staples, sutures, clips, tacks, screws, pins, anchors, fasteners, sheaths, shunts, tissue barriers, stents and grafts. Self sealing implants of the present disclosure may comprise both biodegradable and non-biodegradable materials including those listed above.

Additionally, any part of the implant may include biologically acceptable additives such as catalysts, buffer salts, salts, inorganic fillers, plasticizers, antioxidants, dyes, pigments, image-enhancing agents (MRI, CT, X-ray, and fluoroscopic contrast agents), dilutants, bioactive agents such as pharmaceutical and medicinal agents, and combinations thereof which can be coated on the implant or impregnated within the materials.

In some embodiments, visualization agents including dyes or pigments may be useful to improve visibility during surgical procedures, including visualizing fluid flow through or around the device. Visualization agents may be selected from the among any of the various non-toxic colored substances suitable for use in medical implantable medical devices, such as FD&C BLUE (#1, #2, #3, and #6), eosin, methylene blue, indocyanine green, or colored dyes normally found in synthetic sutures. In embodiments, a color such as green or blue may be desirable and may have better visibility in the presence of blood or on a pink or white tissue background. However, a red dye may be suitable when the underlying tissue is white.

The visualization agent may be present with either reactive component, or, alternatively otherwise incorporated within the reinforcing material or wound closure device. The colored substance may or may not become chemically bound to the hydrogel. The visualization agent may be present in embodiments less than about 1% weight/volume, in other embodiments less than about 0.01% weight/volume, and in yet other embodiments, less than about 0.001% weight/volume concentration.

Medicinal agents which may be incorporated into the implant include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof. Examples of suitable antiseptics and disinfectants which may be combined with the present disclosure include hexachlorophene, cationic biguanides like 25chlorohexadine and cyclohexidine, iodine and iodophores like povidone-iodine, halo-substituted phenolic compounds like PCMX (e.g., p-chloro-m-xylenon, furan medical preparations like nitrofurantoin and nitrofurazone, methanamine, aldehydes like gluteraldehyde and formaldehyde, alcohols, combinations thereof, and the like. In some embodiments, at least one of the antimicrobial agents may be an antiseptic, such as triclosan.

Classes of antibiotics that can be combined with the present disclosure include tetracyclines like minocycline, rifamycins like rifampin, macrolides like erythromycin, penicillins like nafcillin, cephalosporins like cefazolon, beta-lactam antibiotics like imipenen and aztreonam, aminoglycosides like gentamicin and TOBRAMYCIN®, chloramphenicol, sulfonamides like sulfamethoxazole, glycopeptides like vancomycin, quilones like ciproflaxin, fusidic acid, trimethoprim, metronidazole, clindamycin, mupirocin, polyenes like amphotericin B, azoles like fluconazole, and beta-lactam inhibitors like sublactam. Other antimicrobials which may be added include, for example, antimicrobial peptides and/or proteins, antimicrobial polysaccharides, quorum sensing blockers (e.g., brominated furanones), anti-virals, metal ions such as ionic silver and ionic silver glass, surfactants, chemotherapeutic drug, telomerase inhibitors, other cyclic monomers including 5-cyclic monomers, mitoxantrone, and the like.

In some embodiments, suitable bioactive agents which may be used include colorants, dyes, preservatives, protein and peptide preparations, antibodies and nanobodies, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like and combinations thereof.

In some embodiments, polymer drugs (polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS) and the like) may be utilized and combinations thereof.

In certain embodiments, implants of the present disclosure may contain suitable medicinal agents such as viruses and cells, peptides, polypeptides and proteins, analogs, muteins, and active fragments thereof, such as immunoglobulins, antibodies (monoclonal and polyclonal), cytokines (e.g., lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes, viral particles, and combinations thereof. It should be understood that the degradation mechanisms of implants according to the present disclosure may be tailored to provide specific release rates, wherein the degradation of certain materials may correspond to an elution or release of a bioactive agent.

Methods for combining the above mentioned bioactive agents with materials of the present disclosure are within the purview of those skilled in the art and include, but are not limited to, mixing, blending, compounding, spraying, wicking, solvent evaporating, dipping, brushing, vapor deposition, coextrusion, capillary wicking, film casting, molding and the like. Additionally, solvents may be used to incorporate various agents into the implant. Suitable solvents include, but are not limited to, polar and non-polar solvents such as alcohols, e.g., methanol, ethanol, propanol, chlorinated hydrocarbons (e.g., methylene chloride, chloroform, 1,2-dichloro-ethane), and aliphatic hydrocarbons such as hexane, heptene, and ethyl acetate.

Bioactive agents incorporated into implants of the present disclosure may have various release profiles include, but not limited to, zero order, first order, second order release profiles and combinations thereof. It is also within the purview of one skilled in the art to modify materials to be more hydrophobic or hydrophilic to achieve desired bioactive agent release results. As previously mentioned, bioactive agents and materials may both be altered to achieve specific release mechanisms to correspond with the integration of the implant into tissue.

Once the implant is constructed, it can be sterilized by any means within the purview of those skilled in the art including but not limited to ethylene oxide, electron beam (e-beam), gamma irradiation, autoclaving, plasma sterilization and the like.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A self-sealing implant comprising: at least one staple and a polymeric buttress, wherein upon interaction of the at least one staple and the buttress, a hydrogel is formed.

2. The self-sealing implant according to claim 1, wherein at least one of the staple and the buttress further comprises a material selected from the group consisting of succinimidyl containing polymers and multifunctional primary amines.

3. The self-sealing implant according to claim 1, wherein the self-sealing implant further comprises at least one reactive component selected from the group consisting of electrophilic functional groups and nucleophilic functional groups.

4. A method comprising the steps of:
positioning a polymeric buttress comprising a first reactive component on a tissue;
firing at least one staple comprising a second, complementary reactive component from a stapler, the at least one staple contacting the buttress; and,
initiating a chemical reaction.

5. The method according to claim 4, wherein either the first or second complementary reactive components comprise a polymer drug.

6. The method according to claim 4, wherein either the first or second complementary reactive components comprise a medicinal agent.

7. A method comprising the steps of:
positioning a polymeric buttress comprising a first reactive component on a tissue;
firing at least one staple comprising a second, complementary reactive component from a stapler, the at least one staple contacting the buttress; and,
forming a hydrogel.

* * * * *